(12) United States Patent
Reis et al.

(10) Patent No.: US 8,142,378 B2
(45) Date of Patent: Mar. 27, 2012

(54) IMMOBILIZING AND SUPPORTING INFLATABLE SPLINT APPARATUS

(76) Inventors: Daniel Reis, Haifa (IL); Dalia Zucker, Haifa (IL); Asher Bin Nun, Carmiel (IL)

( * ) Notice: Subject to any disclaimer, the term of this patent is extended or adjusted under 35 U.S.C. 154(b) by 684 days.

(21) Appl. No.: 10/797,278

(22) Filed: Mar. 10, 2004

(65) Prior Publication Data

US 2005/0203451 A1 Sep. 15, 2005

(51) Int. Cl.
*A61F 5/00* (2006.01)
(52) U.S. Cl. .......................... 602/13; 602/23
(58) Field of Classification Search .............. 601/15, 601/148–152; 602/13; 128/DIG. 20
See application file for complete search history.

(56) References Cited

U.S. PATENT DOCUMENTS

| | | | | |
|---|---|---|---|---|
| 3,164,152 A | * | 1/1965 | Vere Nicoll | 602/13 |
| 3,901,225 A | * | 8/1975 | Sconce | 602/13 |
| 4,157,713 A | * | 6/1979 | Clarey | 602/13 |
| 5,221,092 A | * | 6/1993 | Simons et al. | 273/348.4 |
| 5,288,286 A | | 2/1994 | Davis et al. | |
| 5,795,312 A | * | 8/1998 | Dye | 601/151 |
| 5,876,364 A | | 3/1999 | Herbst | |
| 5,954,676 A | | 9/1999 | Kramer, III | |
| 5,957,872 A | | 9/1999 | Flick | |
| 6,146,347 A | * | 11/2000 | Porrata | 602/21 |
| 6,315,745 B1 | | 11/2001 | Kloecker | |
| 6,719,711 B1 | | 4/2004 | Islava | |
| 2002/0042585 A1 | | 4/2002 | Kloecker | |
| 2002/0143280 A1 | | 10/2002 | Souney et al. | |
| 2003/0176825 A1 | | 9/2003 | Yavnai | |
| 2003/0191420 A1 | | 10/2003 | Kuiper et al. | |

* cited by examiner

*Primary Examiner* — Michael A. Brown
(74) *Attorney, Agent, or Firm* — Browdy and Neimark, PLLC

(57) ABSTRACT

Disclosed is a medical device which operates as a supporting splint for the treatment of orthopedic conditions. Said device is an inflatable, flexible, lightweight water-resistant splint whose measure of rigidity is easily controlled by the user. According to the present invention there are several embodiments of the splint, each suited to fit a different body part such as the limbs, the torso, the chest and the neck. Said device which is constructed of inflatable tubes is made of two nylon layers soldered together and is coated with polyurethane. The tubes may be inflated by an attachable hand pump or by other means of supplying air pressure. The present invention is especially designed to allow the normal blood circulation to the treated body part, provide ventilation to the area and enable easy inspection of an injury.

23 Claims, 5 Drawing Sheets

IMMOBILIZING AND SUPPORTING INFLATABLE SPLINT APPARATUS

FIELD OF THE INVENTION

The present invention relates to the field of medical devices, and, more particularly, it relates to inflatable versatile/universal multi purpose splints.

BACKGROUND OF THE INVENTION

The traditional techniques of providing support and immobilization in orthopedic conditions revolves around three types of devices: casts, which have application primarily in broken limbs; splints, which are used to immobilize and stabilize the limbs and the torso; and pressure bandages, which help control swelling and give a degree of support. Creative individuals have come up with a variety of departures from these standard themes in order to achieve better patient treatment. Inflatable pouches made from elastic materials exist, adapted to be filed with either liquid or gas, and incorporating means for securing these pouches to the injured part of a human body and tightening them around it. Splints of this kind effect the immobilization and compression of a limb or other part of a human body. One of the alternative devices is presented in U.S. Pat. No. 5,954,676.

This device utilizes two sets of multi-layer deformable materials, such as fiberglass shims located in pouches in first and second members having re-sealable bladders of sheaths that provide structural support on each side of the limb.

The main drawback of the device, which limits its application considerably, relates to its fixed and inflexible shape that does not take into consideration the rounded form of the limbs, joints and the torso, for instance.

A different device is U.S. Pat. No. 5,288,286, which is an adjustable pressure cast for orthopedic injuries. It is composed of three sets of air chambers and is only designed for treating orthopedic leg injuries such as fractures. As in the previous patent, this device suffers from an inconvenient structure, which may only support the calf, the ankle and the foot of a patient without conforming to the shape of these structures.

There is a need for a method and a concept for a light and convenient splint which adjusts to the shape of the limb, joints or any other body part in question and may also provides steady support to the trunk (i.e. spine, ribs, neck etc.), while at the same time allowing free blood circulation, ventilation and enables medical inspection of the injured area.

SUMMARY OF THE INVENTION

In accordance with the shortcomings of previous art, it is a principal object of the present invention to provide a splint device which will present a maximum adjustment range, so it can be easily and securely fitted to the injured body part, without bringing about any uncomfortable chafing and minimize the overall discomfort, will also allow for adequate blood circulation to the injured part, and support the joints in an optimal position with a controllable measure of rigidity.

It is yet another object of the present invention to introduce a multi purpose splint that will be appropriate for the treatment of a wide range of conditions, such as fractures and sprains and post-operative support, prevent bedsores and allow inspection of various wounds. It provides a handy solution for the temporary support of an injured limb in field conditions while transporting a patient, for example, can also be used as a long term cast or bandage in the full course of treatment and may give postoperative support.

The said splint offers solutions for the setting and treatment of various areas of the body, such as the neck, the limbs, spinal and chest areas. It answers the basic need for a simple device, which is easy to use, handle, store and transport.

It is yet another object of the present invention to offer a practical solution to the needs of various medical teams such as hospital staff, EMS, health and care for the elderly, army and police emergency teams as well as private home use.

The invention describes a splint designed to allow for an adjustable and comfortable fit to different parts of the body which achieves maximum comfort and facilitates the recuperation period. It is a simply structured splint, which allows for uncomplicated assembly and operation. The splint is designed to fit the shape of the body part in need of treatment it provides support and wrapping for the injured area from three sides. The splint is made out of inflatable ribs. Using a hand pump or an air pressure source tank the ribs may be inflated to various degrees that provide the optimum support and comfort required for the particular conditions. Ventilation holes in the structure allow for sufficient airing and circulation of the limb and body part and the treated area. The splints are secured into place by Velcro straps.

The simplicity of the design and assembly enable the patients themselves to assemble and adjust the splint.

BRIEF DESCRIPTION OF THE DRAWINGS

These and further features and advantages of the invention will become more clearly understood in the light of the ensuing description of a preferred embodiment thereof, given by way of example only, with reference to the accompanying drawings, wherein—

DETAILED DESCRIPTION OF THE INVENTION

The present invention is a new and simple medical device, aimed to help treat orthopedic conditions, by supporting and splinting immobilizing the injured body part in a desired position. It is a comfortable to wear lightweight device, which is simple, easy to assemble, water resistant and demands very little storage space. This is a multipurpose device facilitating emergency and long term treatments of different sorts of conditions. The preferred embodiments of the invention are inflatable and adjustable, suited to fit different body part including the limbs, the chest, the torso, spine and the neck. The measure of air pressure inflating the device and the manner of fastening it around a body part are controllable and may be adjusted to suit the specific needs of any given condition. The device is made from a double layer of nylon coated by polyurethane, a flexible and a light weight material which is also strong and waterproof.

Figure 1:
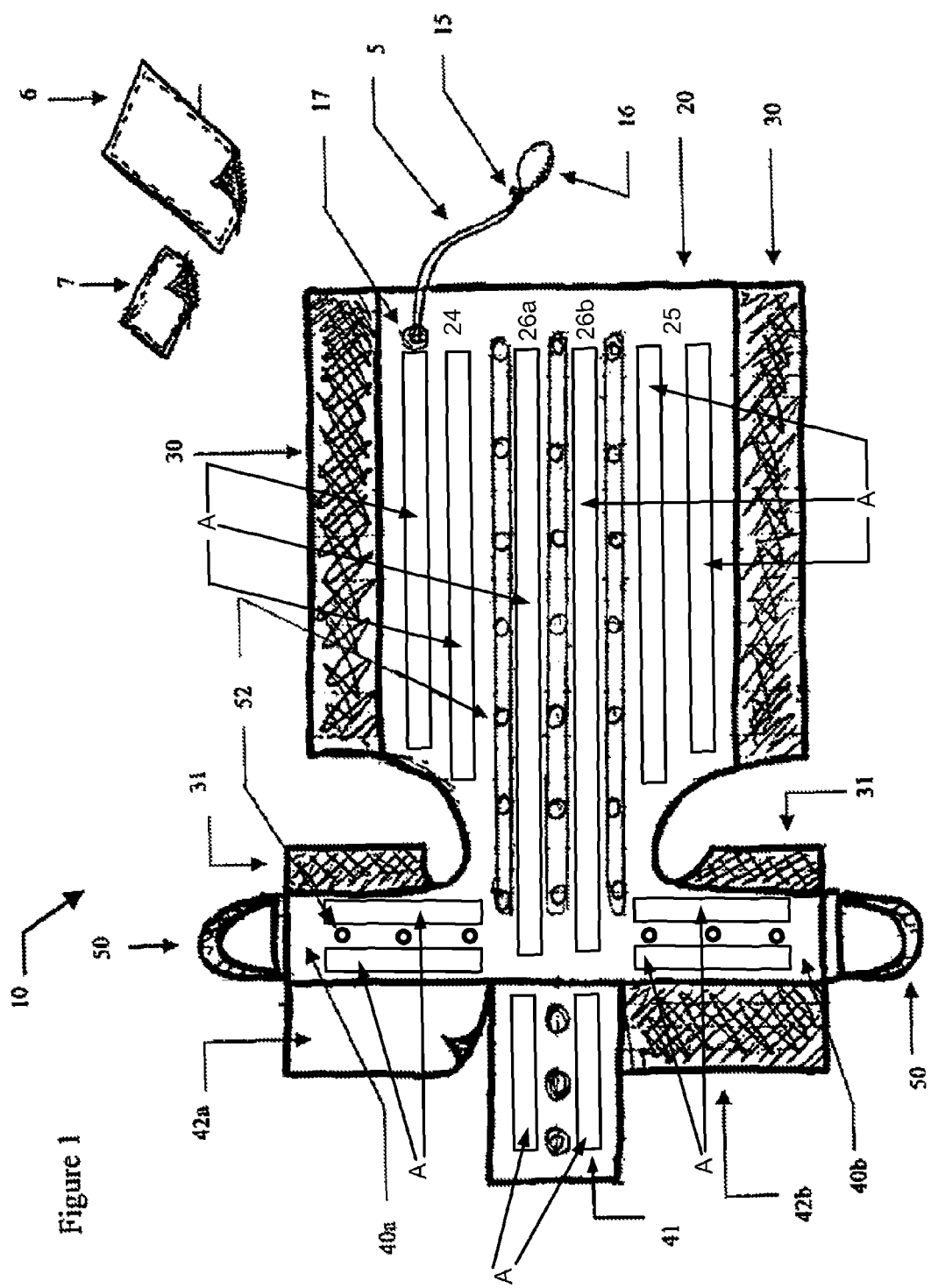
FIG. 1 is a perspective view of a first embodiment of the invention in an unassembled and un-inflated condition.
Figure 2:
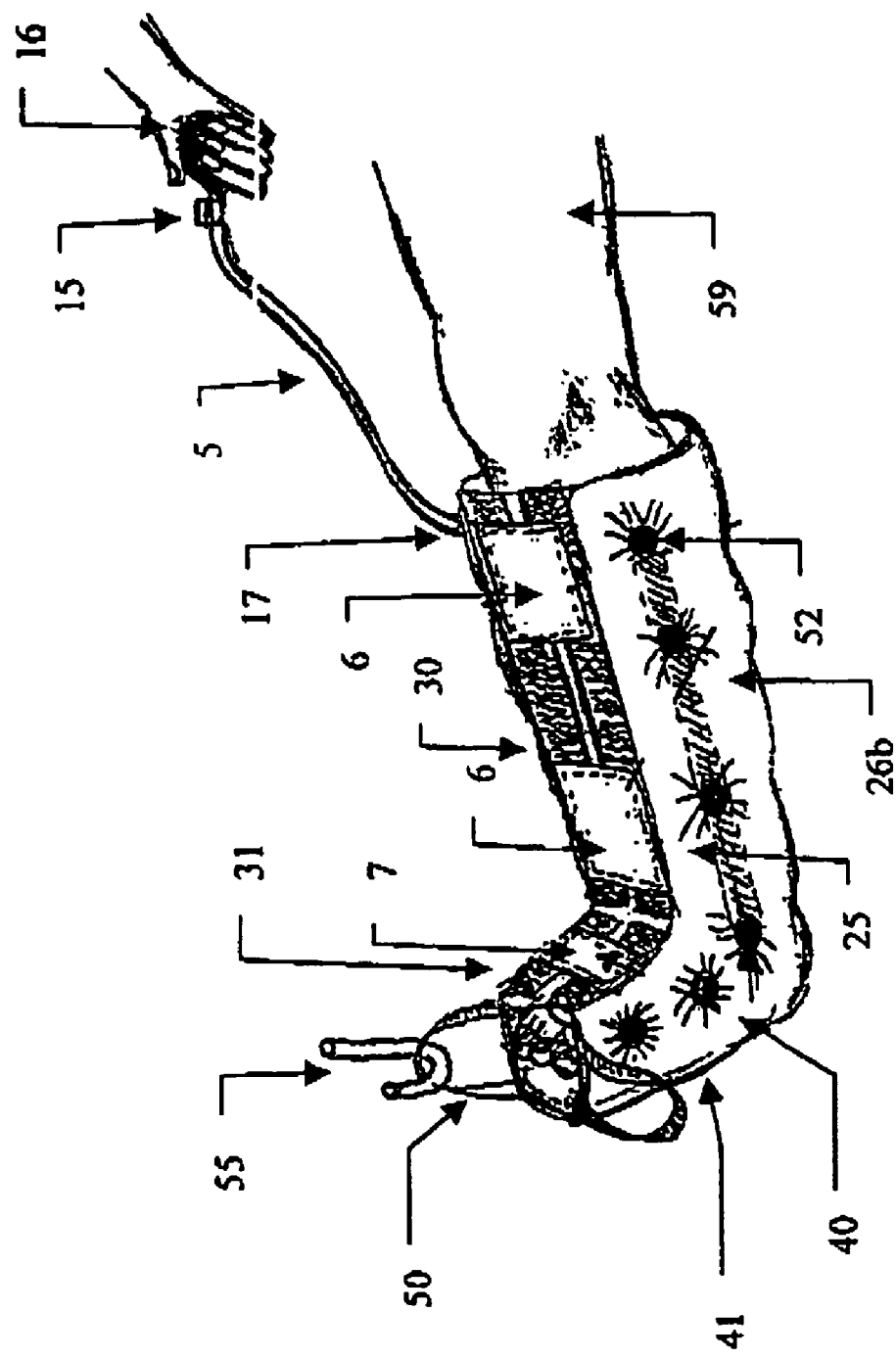
FIG. 2 illustrates the first embodiment of the invention assembled on a leg.

FIG. 1 offers a general description of the first embodiment of the invention, suited for leg injuries, in an unassembled condition. The splint 10 is comprised of a main body 20 and two or more unattached adjustable straps: a front upper strap 6 and a front lower strap 7. When in use, parts 24, 25, 26a, 26b wrap the leg from three sides: part 24 holds the left side of the leg and part 25 the right side, while the back of the leg is wrapped by the splint central part 26a, 26b. Connecting Velcro surfaces 30 and 6 fastens the device around the calf. The lower right 40a and left part 40b of the splint wraps around the foot, while part 41 covers the sole of the foot. Attaching Velcro straps 31 to strap 7 on top of the foot and strap 42a to 42b at the sole fastens the lower part of the splint for supporting the lower part of the foot. FIG. 2 illustrates the device as it is assembled on a leg 59.

Both the lower and the upper part of the splint have ventilating holes 52 to increase the comfort of long term use of the device, and at the edge of parts 40a, 40b, there are loops 50 which, if necessary, allow for suspending the leg raised up on a hook 55 to prevent it from swelling, as illustrated in FIG. 2. Parts 24, 25, 26, 40, 41 contain inflatable tubes, shown at locations A. These tubes are designed to wrap the leg, the foot the ankle and the heel of the injured, taking into account the leg's curves and structure for maximum compatibility. Using the hand pump 16, which is connected to the said tubes through pipe 5 and valve 17, the tubes in the splint may be inflated. Alternatively, an air pressure source can be connected to valve 17 and used for the same purpose. Once inflated, valve 15 may be used to open the airways and let the air out of the tubes. Combining the effect of the hand pump 16 and the valve 15 allows for achieving the desired pressure in the tubes resulting in the required stiffness of the splint 10 around the leg, so that the support needed is maintained and the movement and flexibility of the leg is controlled without causing unnecessary discomfort. The pressure that the air tubes create on the leg does not obstruct the blood flow to the leg, and the ventilation holes 52 allow for sufficient airing of the area. When inflated, the splint takes up the shape of the part of the body for which it was designed as FIG. 3 illustrates.

Additional control over the amount of pressure and the tightness of the splint on the leg may be achieved by the fastening or loosening of the Velcro straps 6,7 to splint Velcro 30 and 31 respectively. In a different embodiment Velcro straps 6 and 7 are stitched to one of the sides of the splint body 20. As illustrated in FIG. 2 the patients can easily reach the said straps since they are on the front side of the leg, and has a convenient access to the pump so he or she can adjust level and volume of splint air pressure for themselves, to achieve maximum results.

Figure 3:
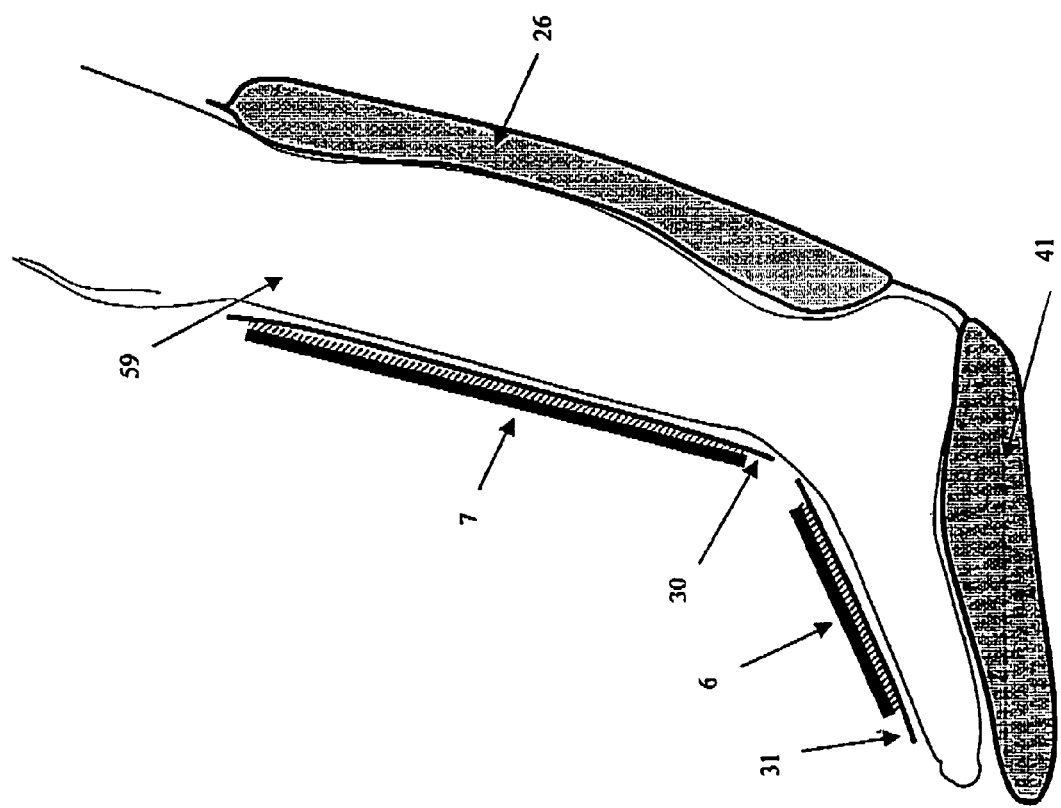
FIG. 3 is a cross-sectional view of the assembled splint shown in FIG. 2.

FIG. 3 illustrates a cross section of the splint as it is assembled on a leg 59. In this illustration it is easy to see that the splint is designed to fit the structure of the body part (the leg 59, in this example) and its joints.

The second embodiment of the invention is illustrated in FIGS. 4, 5, 6 and 7. It is designed to be assembled on an arm. The principles guiding the structure of this embodiment are similar to those of the first embodiment; it differs from the first only to fit the structure and the treatment of a human arm.

Figure 4:
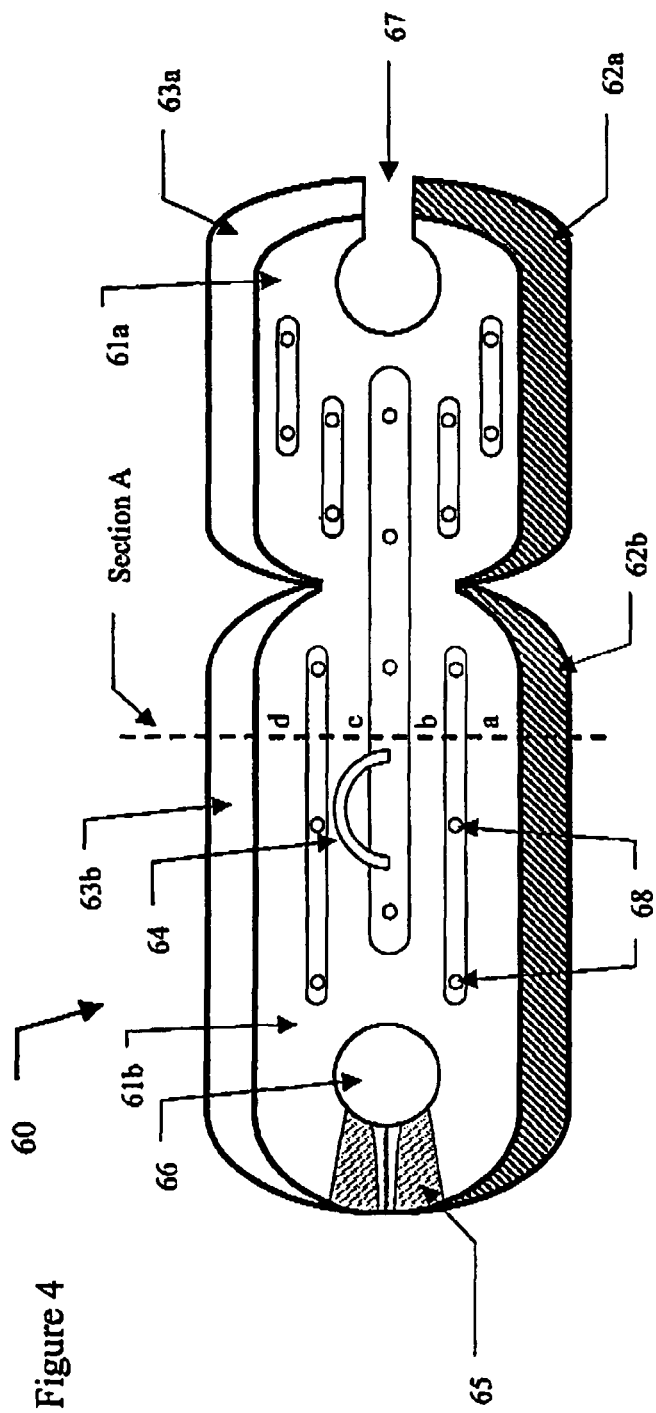
FIG. 4 illustrates perspective view of a second embodiment of the invention in an unassembled and un-inflated condition.

FIG. 4 illustrates the second embodiment in an unassembled state. The main body of the splint is divided into two parts: for supporting the upper part of the arm 61a (between the shoulder and the elbow) and of the lower part of the arm 61b (between the elbow and the wrists). Enclosing the main body 61 are Velcro straps 62, 63 which connect to each other when the device is assemble on an arm. The main part 61a contains an aperture for the shoulder 67 and the main part 61b includes an aperture for the palm 66 and a supporting surface for the palm and hand 65.

Figure 5:
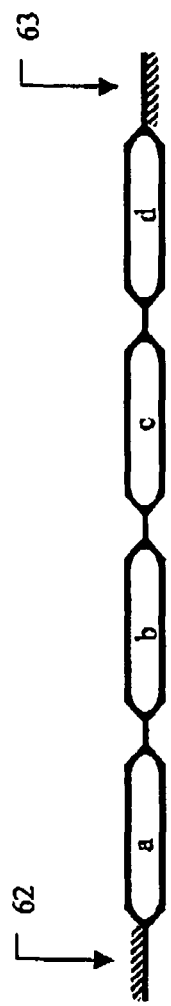
FIG. 5 illustrates a cross sectional view (section A) of the second embodiment as illustrated in FIG. 4.

Like the main body of the first embodiment these two sections are both comprised of inflatable tubes which, when assembled on the arm, are designed to support the arm from three directions. FIG. 5 displays a cross-section of the splint when it is inflated and unassembled. This figure clearly shows the four tubes in the splint Velcro straps 62, 63 connect when the splint is assembled.

Figure 6:
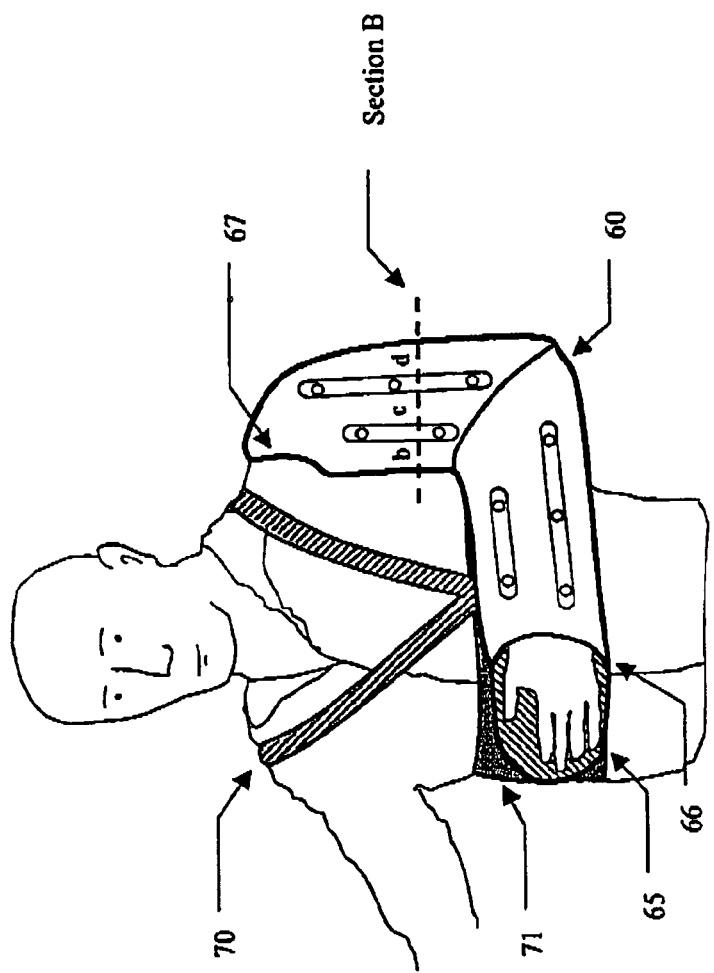
FIG. 6 illustrates the second embodiment of the invention assembled on an arm.

Also in FIG. 4 are the ventilating holes 68, similar to the ones on the first embodiment of this invention 52, and a support strap clip 64. This clip enables the attachment of straps that transfer the weight of the hand to the shoulders or to the waist. FIG. 6 illustrates the splint assembled on an arm. The figure displays the two options of attaching the supporting straps: a suspension strap 70 around the patience's neck and a strap wrapped around the waist 71.

The straps hook to the splint via the said clip 64.

Figure 7:
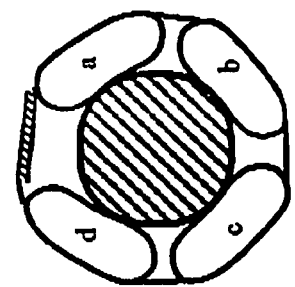
FIG. 7 illustrates a cross sectional view (section B) of the second embodiment as illustrated in FIG. 6.

FIG. 6 also clearly illustrates the function of the aperture of the shoulder 67, the palm's aperture 66 and of the supporting surface for the palm 65. The structure of this embodiment of the splint is suited to hold the arm in a comfortable 90 degree angle at the elbow. FIG. 7 illustrates the cross section B of the assembled splint. This figure shows that the splint provides pressure and support to the arm from four directions.

Another embodiment of the present invention is a vest splint, designed to support the rib cage. The inflatable ribtubes of the splint are aligned to follow the inclination of the rib bones and may be inflated in sections according to necessity. The vest is wrapped around the chest leaving two apertures for the arms and is fastened in the front by Velcro straps. These unique designs of the splints as described allows for setting and stabilizing the injured body part while providing a controlled range of flexibility. Providing necessary support to the area and improving the course of treatment for better results.

While the above description contains many specifities, these should not be construed as limitations on the scope of the invention, but rather as exemplifications of the preferred embodiments. Those skilled in the art will envision other possible variations that are within its scope. Accordingly, the scope of the invention should be determined not by the embodiment illustrated, but by the appended claims and their legal equivalents.

What is claimed is:

1. A splint for immobilizing and supporting a body part of a human, wherein said splint comprises:
   a) an inflatable main body structured to fit a shape and structure of a body part to be immobilized being composed of a leg having a curvature, a foot, an ankle and a heel, the inflatable main body comprising integrally made parts, which include leg parts for holding left and right sides of the leg, a part for wrapping a back of the leg, and a foot part for wrapping ankle and sole portions of the foot, to cover the body part from three sides, leaving one side uncovered, the shape of the inflatable main body defining a curvature corresponding to the foot part of the leg between the ankle and sole portions, the inflatable main body comprising inflatable tubes for achieving variable degrees of support, stiffness and restriction of movement, said inflatable main body being made of a flexible material having two opposed edges, wherein said shape of the inflatable main body and arrangement of said inflatable tubes within said integrally made parts of the main body being such that when said tubes are inflated, the main body takes up the shape of said body part to provide maximum compatibility and prevent pressure on the heel, the integrally made ankle, foot and sole parts of the splint comprising the inflatable tubes containing parts arranged such that when the splint wraps the leg, the inflatable tubes containing parts extend along respectively the ankle, foot and sole;

b) at least one gas pressure source device connected to said splint; and c) at least one adjustable member for connecting said two opposed edges together across said uncovered side of the body part in a manner to allow adjustment of the pressure and tightness of said splint on the body part.

2. The splint according to claim 1, wherein said at least one adjustable member is a strap made of a hook-and-loop material.

3. The splint according to claim 1, wherein said splint is made of two nylon layers joined together by soldering means.

4. The splint according to claim 1, wherein said splint is made of two nylon layers which are coated with polyurethane.

5. The splint according to claim 1, wherein the pressure source device is a hand pump.

6. The splint according to claim 1 wherein the tightness of the splint on the body part is controlled by the fastening or loosening of the at least one adjustable member.

7. The splint according to claim 6, wherein said at least one adjustable member is a strap made of a hook-and-loop material.

8. The splint according to claim 1 further including a suspension strap.

9. The splint according to claim 1 wherein pressure within the splint is controlled by a valve.

10. The splint according to claim 1 wherein the adjustable member is detachable.

11. The splint according to claim 1, further comprising at least one loop connected for suspension purposes.

12. The splint according to claim 11, wherein said at least one loop is connected at one of said edges.

13. A splint according to claim 1, comprising ventilation holes for skin ventilation contained in, and extending between the inflatable tube containing parts.

14. A splint according to claim 1, wherein inflation of said inflatable tubes fits the structure of the inflatable main body to the structure of the three sides of the body part covered by the inflatable main body.

15. A splint according to claim 1, wherein said inflatable main body is shaped to follow closely the shape of the body part when inflated.

16. A splint for immobilizing and supporting a body part of a human, wherein said splint comprises:

a) an inflatable main body structured to fit a shape and structure of a body part to be immobilized being composed of a leg having a curvature, a foot, an ankle and a heel, the inflatable main body comprising integrally made parts, which include leg parts for holding left and right sides of the leg, a part for wrapping a back of the leg, and a foot part for wrapping ankle and sole portions of the foot, to cover the body part from three sides, leaving one side uncovered, the shape of the inflatable main body defining a curvature corresponding to the foot part of the leg between the ankle and sole portions, the inflatable main body comprising inflatable tubes for achieving variable degrees of support, stiffness and restriction of movement and ventilation holes for skin ventilation contained in and extending between the inflatable tube containing parts, said inflatable main body being made of a flexible material having two opposed edges, wherein said shape of the inflatable main body and arrangement of said inflatable tubes within said integrally made parts of the main body being such that when said tubes are inflated, the main body takes up the shape of said body part to provide maximum compatibility and prevent pressure on the heel.

17. The splint according to claim 16, wherein the integrally made ankle, foot and sole parts of the splint comprise the inflatable tubes containing parts arranged such that when the splint wraps the leg, the inflatable tubes containing parts extend along respectively the ankle, foot and sole.

18. The splint according to claim 16, wherein said splint is made of two nylon layers joined together by soldering means.

19. The splint according to claim 16, wherein said splint is made of two nylon layers which are coated with polyurethane.

20. The splint according to claim 16 wherein the tightness of the splint on the body part is controlled by the fastening or loosening of the at least one adjustable member.

21. The splint according to claim 16 further including a suspension strap.

22. A splint according to claim 16, wherein inflation of said inflatable tubes fits the structure of the inflatable main body to the structure of the three sides of the body part covered by the inflatable main body.

23. A splint according to claim 16, wherein said inflatable main body is shaped to follow closely the shape of the body part when inflated.

* * * * *